United States Patent [19]

Nakano et al.

[11] Patent Number: 5,001,289
[45] Date of Patent: Mar. 19, 1991

[54] SHAPED ZEOLITE CATALYST FOR LIQUID PHASE ORGANIC REACTIONS

[75] Inventors: Masao Nakano, Hikari; Kazuhiko Sekizawa, Shinnanyo; Toshio Hironaka, Tokuyama; Kiyotaka Oyama; Seiichi Asano, both of Hikari, all of Japan

[73] Assignee: Tosoh Corporation, Shinnanoyo, Japan

[21] Appl. No.: 384,050

[22] Filed: Jul. 24, 1989

Related U.S. Application Data

[63] Continuation of Ser. No. 139,273, Dec. 29, 1987, abandoned.

[30] Foreign Application Priority Data

Dec. 29, 1986 [JP] Japan .................... 61-310171

[51] Int. Cl.$^5$ ............... C07C 17/12; C07C 25/00
[52] U.S. Cl. ..................... 570/208; 423/328; 502/60; 502/79; 570/206
[58] Field of Search ........... 570/206, 208; 502/79, 502/527, 60; 423/328

[56] References Cited

U.S. PATENT DOCUMENTS

| | | | |
|---|---|---|---|
| 3,386,802 | 6/1964 | Michalka | 423/328 |
| 3,431,218 | 3/1969 | Plank et al. | 502/79 |
| 4,249,903 | 2/1981 | Smalka et al. | 23/313 R |
| 4,404,416 | 9/1983 | Adams et al. | 502/527 |
| 4,794,201 | 12/1988 | Higuchi et al. | 570/208 |
| 4,822,933 | 4/1989 | Suzuki et al. | 570/208 |

FOREIGN PATENT DOCUMENTS

| | | | |
|---|---|---|---|
| 011272 | 7/1984 | European Pat. Off. | 570/208 |
| 118851 | 9/1984 | European Pat. Off. | |
| 28599 | 3/1978 | Japan | 423/328 |
| 1047943 | 11/1966 | United Kingdom | 423/328 |
| 1124524 | 8/1968 | United Kingdom | 423/328 |

OTHER PUBLICATIONS

T. M. Wortel et al.: Selective Bromination of Halobenzenes using Zeolite Catalyst, Journal of Catalysis, pp. 110–120 (1979).

*Primary Examiner*—Werren B. Lone
*Attorney, Agent, or Firm*—Cushman, Darby & Cushman

[57] ABSTRACT

Disclosed is a shaped zeolite catalyst used for liquid phase organic reactions. The shaped zeolite catalyst is composed of substantially spherical particles having a particle diameter substantially in the range of from 70 to 300 μm, and which has fine pores having a pore volume of 0.4 to 1 cc per gram of the shaped catalyst and a median pore diameter based on the pore volume of 1,000 to 5,500 Å.

11 Claims, No Drawings

SHAPED ZEOLITE CATALYST FOR LIQUID PHASE ORGANIC REACTIONS

This is a continuation of application Ser. No. 07/139,273, filed Dec. 29, 1987, which was abandoned upon the filing hereof.

BACKGROUND OF THE INVENTION (1) Field of the Invention

The present invention relates to a shaped zeolite catalyst for liquid phase organic reactions. More particularly, it relates to a shaped zeolite catalyst which is used in a suspended bed for a liquid phase organic reaction.

(2) Description of the Related Art

Serious research is being carried out into the application of various solid catalysts to liquid phase organic reactions, and zeolites have attracted attention for use as a solid acid catalyst or solid base catalyst. As the liquid phase organic reaction to which a zeolite catalyst is applied as the solid catalyst, there can be mentioned benzylation of an alcohol (Chemistry Letters, 1101, 1983), N-monoalkylation of anilines (Chemistry Letters, 1783, 1982), and halogenation of a benzene derivative. Examples of the halogenation of a benzene derivative by using a zeolite catalyst are disclosed in Journal of Catalysis, 60, 110 (1979), Japanese Unexamined Patent Publication No. 59-130,227, Japanese Unexamined Patent Publication No. 59-144,722 and Japanese Unexamined Patent Publication No. 59-163,329. However, only the catalytic activity of zeolite powders is taught in these prior art references.

The as-prepared zeolite is generally a crystalline fine powder. Accordingly, if the as-prepared zeolite is directly used as a catalyst, for example, in a fixed bed, a pressure loss occurs or separation or recovery of the catalyst for preventing incorporation of the catalyst into the product after the reaction becomes difficult, and therefore, industrially, the zeolite is often used after granulation. The shapes and dimensions desired for a shaped catalyst obtained by granulation of a powdery catalyst differ according to the application mode of the catalyst. In the reaction using a fixed bed (packed bed), which is most popular for the catalytic reaction, a small pressure loss and a uniform circulation of the reactants are desired, and the powdery catalyst is generally used in the form of a granulated product having a relatively large size (the particle diameter is about 1 to about 5 mm) such as a compression-molded form, an extrusion-molded form or a rolling granulated form. In the reaction using a fluidized bed, to maintain good fluidization, the catalyst is desired to have a high mechanical strength, a spherical shape without angles and having a smooth surface, and therefore, a shaped form having a relatively small size, such as a spray-dried granule or a granule molded in an oil, is used. For example, a spray-dried granule having an average particle diameter of 50 to 70 μm is used as an FCC (fluidized catalytic cracking of a hydrocarbon) catalyst. In view of the catalyst life, preferably the mechanical strength of the shaped catalyst is high. However, an increase of the mechanical strength generally results in reduction of the average pore diameter of the catalyst and a degradation of the catalytic activity. Accordingly, it is not easy to obtain a shaped catalyst having a sufficient strength and a sufficient catalyst activity in combination.

As is apparent from the prior art references, solid catalysts, especially many zeolite catalysts, are applied to liquid phase organic reactions. In this case, since the reaction is a liquid-solid two-phase reaction or a gas-liquid-solid three-phase reaction, in order for the zeolite catalyst to act effectively in the reaction system, preferably the zeolite catalyst be uniformly suspended in the liquid phase. Furthermore, at the step of separating and recovering the zeolite catalyst, the zeolite catalyst should be promptly sedimented in the reaction liquid, that is, the separability of the zeolite catalyst from the reaction liquid should be good.

However, when the powdery zeolite is directly used as a catalyst for a liquid phase reaction, problems often occur at the step of separating and recovering the catalyst after the reaction, and therefore, when the zeolite is used as a catalyst on an industrial scale, the zeolite powder should be granulated and then used as a catalyst. However, the suspensibility, sedimentability, and mechanical strength of the shaped zeolite catalyst in a liquid phase suspended bed reaction have not been investigated, and the optimum properties thereof have not been clarified.

Under this background, we made research with a view to developing a practical zeolite catalyst applicable to a liquid phase organic reaction, especially a liquid phase halogenation of benzene and/or benzene derivatives. As the result, it was found that if the zeolite powder is used directly in the form of a powder for the above-mentioned reaction, the sedimentability of the catalyst in the reaction liquid after the reaction is poor and, therefore, it takes a long time to separate the catalyst from the reaction liquid and it is difficult to recover and handle the separated catalyst. It also was found that, in the case of a continuous reaction, a problem of flow-out of the catalyst to the outside of the reactor arises. Accordingly, a compression-molded form, extrusion-molded form or rolling granulated form having a diameter of about 3 to about 5 mm, customarily used for the gas phase fixed bed reaction, was used for the above-mentioned reaction. It was found that although the catalyst can be easily separated, but because of a relatively large particle diameter of the above-mentioned shaped form, it was difficult to suspend the catalyst uniformly in the reaction liquid phase and the catalyst did not act effectively during the reaction. In the case of a spray-dried granule having an average particle diameter of 50 to 70 μm, such as an FCC catalyst, it was found that the sedimentability of the product in the reaction liquid was poor and the separation of the catalyst from the reaction liquid was difficult and in the continuous reaction, a problem of flow-out of the catalyst arose as in the above-mentioned case.

SUMMARY OF THE INVENTION

We found that a shaped zeolite catalyst composed of substantially spherical particles having a particle diameter substantially in the range of 70 to 300 μm, and which has fine pores having a pore volume of 0.4 to 1 cc per gram of the shaped catalyst and a median pore diameter based on the pore volume of 1,000 to 5,500 Å, is uniformly suspended in the reaction liquid phase at the reaction step, has a high activity, is easily separated and recovered with a good sedimentability and has a sufficiently high mechanical strength and a long catalyst life.

Thus, in accordance with the present invention, there is provided a shaped zeolite catalyst for liquid phase organic reactions, which is composed of substantially spherical particles having a particle diameter substantially in the range of 70 to 300 μm, and which has fine pores having a pore volume of 0.4 to 1 cc per gram of the shaped catalyst and a median pore diameter based on the pore volume of 1,000 to 5,500 Å.

DESCRIPTION OF THE PREFERRED EMBODIMENTS

The zeolite is ordinarily called a crystalline aluminosilicate and the skeleton is composed of $SiO_4$ tetrahedrons and $AlO_4$ tetrahedrons. It is known that there are many kinds of zeolites in which the bonding of the tetrahedrons differs. Since different kinds of zeolites have different crystal structures, they can be discriminated by the X-ray diffractometry. Many natural and synthetic zeolites are known. For example, there can be mentioned A type zeolite, chabazite, erionite, clinoptirolite, ferrierite, ZSM-5, ZSM-11, mordenite, faujasite and L type zeolite. The kind of the zeolite used in the present invention is not particularly critical. However, since an effective zeolite catalyst differs according to the kind of the reaction, an appropriate zeolite is selected according to the kind of the reaction. In the above-mentioned prior art references, it is taught that L type zeolite or Y type zeolite is preferred for the liquid phase halogenation of benzene derivatives.

Where the zeolite powder is granulated, since the shapability is poor when the zeolite is used alone, to increase the mechanical strength of the shaped catalyst, preferably a clay such as acid clay or bentonite or silica is used as the binder. The amount added of the binder is up to 80% by weight, preferably 2 to 30% by weight.

The spray-drying granulation method can be mentioned as the method for obtaining the shaped zeolite catalyst of the present invention at a high efficiency. According to the spray-drying granulation method, a zeolitecontaining slurry is sprayed in hot air to form liquid drops and these liquid drops are dried. As the method for forming liquid drops by spraying, there can be mentioned an atomizer method and a nozzle method, but the method for forming liquid drops is not particularly critical in the present invention. Conditions ordinarily adopted in the spray-drying granulation method can be adopted in the present invention, but to prepare the shaped zeolite catalyst of the present invention, it is necessary to use a wet-pulverized slurry in which not more than 10% by weight of particles based on the total particles have a particle diameter of at least 30 μm as measured by the Coulter counter method. In the amount of particles having a particle diameter of at least 30 μm is larger than 10% by weight, a shaped catalyst having a large pore volume or pore diameter is obtained and the mechanical strength is reduced. The solid concentration in the slurry is 20 to 60% by weight, and the spray-drying granulation is performed by using hot air maintained at 60° to 200° C.

Preferably the obtained shaped catalyst is used for a liquid phase organic reaction after calcination at 250° to 900° C., especially 300° to 850° C. If the calcination temperature is lower than 250° C., it is sometimes impossible to increase the mechanical strength of the shaped catalyst, and if the calcination temperature is higher than 900° C., there is a risk of destruction of the zeolite structure.

The first characteristic feature of the shaped zeolite catalyst to be used for a liquid phase organic reaction in suspended bed according to the present invention is that the particles have a substantially spherical shape and the particle diameter is substantially in the range of 70 to 300 μm. By "the particle diameter substantially in the range of 70 to 300 μm", is meant that particles occupying at least 90% by weight, preferably at least 95% by weight, of the whole shaped zeolite catalyst have a particle diameter in the range of from 70 to 300 μm. The zeolite catalyst formed body having this particle size range can be directly obtained by granulation. However, if particles are present having a size outside the above-mentioned range, the shaped catalyst having the intended particle diameter range can be obtained by sieving or the like. The particle diameter distribution can be determined according to the microscope method, the sieving method or the like. If the particle diameter is smaller than 70 μm, the sedimentation velocity in the reaction liquid is low and separation or recovery of the catalyst is difficult. If the particle diameter is larger than 300 μm, it is difficult to disperse the catalyst uniformly in the liquid phase at the reaction step, and the catalyst does not act effectively.

The second characteristic feature of the shaped zeolite catalyst is that the fine pore volume is in the range of 0.4 to 1 cc per gram of the shaped catalyst and the median pore diameter based on the pore volume is in the range of 1,000 to 5,500 Å. The pore volume and median pore diameter distribution used herein are determined by a mercury pressure porosimeter which is capable of measuring on pores having a pore diameter of 100 to 75,000 Å. If the pore volume of fine pores is smaller than 0.4 cc per gram of the shaped catalyst, the catalytic activity is low, and if the pore volume is larger than 1 cc per gram of the shaped catalyst, the mechanical strength is low and the catalyst life is short. If the median pore diameter based on the pore volume is smaller than 1,000 Å, the catalytic activity is low, and if the median pore diameter is larger than 5,500 Å, the mechanical strength is low and the catalyst life is short.

The shaped zeolite catalyst of the present invention is often used in a suspended bed for a liquid phase organic reaction. The reaction may be a liquid-solid two-phase reaction or a gas-liquid-solid three-phase reaction. At the reaction step, the shaped zeolite catalyst is uniformly dispersed in the liquid phase by stirring or bubbling of a gas. The reaction may be carried out batchwise, semibatchwise or in continuous manner.

The kind of the liquid phase organic reaction is not particularly limited. For example, liquid phase halogenation of benzene or benzene derivatives can be mentioned. The benzene derivatives include compounds in which a hydrogen atom of benzene is substituted by a halogen or an alkyl group, such as halogenated benzenes and alkylbenzenes. For example, there can be mentioned benzene, monofluorobenzene, monochlorobenzene (MCB), monobromobenzene, monoiodobenzene, toluene and ethylbenzene. An elementary halogen can be used as the halogenating agent. For example, there can be mentioned chlorine, bromine and iodine.

The reaction apparatus, process and conditions employed for the liquid phase halogenation of benzene or benzene derivatives are not particularly limited, provided that benzene or benzene derivatives are brought in contact with the shaped zeolite catalyst. For example, the reaction apparatus may be batchwise, semi-batchwise or continuous. The halogenation reaction can be carried out in a liquid reaction medium, e.g., carbon tetrachloride, which does not exert a harmful influence on the halogenation reaction. Where the liquid reaction medium is employed, the concentration of benzene or benzene derivatives in the reaction medium is in the range of 5 to 99% by weight, preferably 20 to 99% by weight. If the concentration of benzene or benzene derivatives is lower than 5% by weight, the reactants are not sufficiently contacted with the shaped zeolite catalyst and thus the conversion becomes low. When a halogenating agent is continuously supplied to the reaction system, the halogenating agent can be accompanied by an inert gas such as nitrogen, helium or carbon dioxide. The concentration of the halogenating agent in the inert gas/halogenating agent mixture may be 5 to 99%, preferably 20 to 99%.

Where a batchwise or semi-batchwise reaction apparatus is used, the shaped zeolite catalyst is used in the form of a suspension in the reaction liquid. The amount of the shaped zeolite catalyst is 0.001 to 1 kg/l-reaction, preferably 0.005 to 0.1 kg/±-reaction liquid. If the amount of the catalyst is smaller than 0.001 kg/l-reaction liquid, the conversion is low. If the amount of the catalyst exceeds 1 kg/l-reaction liquid, the increase of the conversion becomes minor with an increase of the amount of the catalyst. When a halogenating agent is continuously supplied, the amount of the halogenating agent may be in the range of 1 to 1,500 mol/kg-cat.·hr, preferably 10 to 800 mol/kg-cat. ·hr. If the amount of the halogenating agent is smaller than 1 mol/kg-cat.·hr, the rate of halogenation is low, and, if it exceeds 1,500 mol/kg-cat.·hr, the amount of the unreacted halogenating agent in the reaction mixture undesirably increases.

Where a continuous reaction apparatus is employed, the liquid reactants can be supplied in an amount of 0.5 to 300 l/kg-cat.·hr, preferably 2 to 100 l/kg-cat.·hr. The other reaction conditions may be similar to those employed where a batchwise or semi-batchwise reaction apparatus is used.

The reaction temperature and reaction pressure are not particularly limited, provided that benzene or benzene derivatives are maintained in a liquid state. The reaction temperature is preferably in the range of 0° to 200° C., more preferably 20° to 150° C. If the reaction temperature is higher than the boiling point of the benzene or benzene derivative used, the reaction pressure is increased.

The shaped zeolite catalyst of the present invention is uniformly dispersed at the reaction step and shows a high activity in a liquid phase organic reaction, and the shaped zeolite catalyst of the present invention is promptly sedimented at the catalyst-separating step and is easily separated and recovered. Moreover, the shaped zeolite catalyst of the present invention has a high mechanical strength and a long catalyst life. Furthermore, in the case of the continuous reaction, the problem of flow-out of the catalyst does not arise while the above-mentioned effects are similarly attained. As is apparent from the foregoing description, if the shaped zeolite catalyst of the present invention is used, the liquid phase organic reaction can be carried out at a high efficiency and economically advantageously. Therefore, the present invention is very significant from the industrial viewpoint.

The present invention will now be described in detail with reference to the following examples that by no means limit the scope of the invention. In the examples, % and parts are by weight unless otherwise specified.

EXAMPLE 1

In water, 100 parts of a powder of commercially available L type zeolite (supplied by Tosoh) was sufficiently mixed with 25 parts of acid clay (supplied by Mizusawa Kagaku) to obtain a slurry having a solid concentration of 35%. The slurry was wet-pulverized by passing the slurry through a super mill (supplied by Inoue Seisakusho) so that the residence time was 3 minutes. When the particle size distribution of the solids was measured by a Coulter counter, it was found that the amount of particles having a particle diameter of at least 30 $\mu$m was 7%. The wet-pulverized slurry was introduced at a feed rate of 500 cc/min into an atomizer type spray-drying granulator to obtain a granular form. The rotation number of the atomizer was 4,900 rpm, the diameter of the atomizer was 12 cm, the temperature of hot air at the inlet was 80° C., and the temperature of hot air at the outlet was 53° C. In a muffle furnace, the temperature was gradually elevated and the granular form was maintained at a final temperature of 600° C. for 1 hour to effect calcination. A catalyst A having a particle diameter of 74 to 297 $\mu$m (74−177 $\mu$m=43.5%, 177−297 $\mu$m=56.5%) was obtained by sieving.

When the catalyst A was measured by a mercury pressure porosimeter (Poresizer 9310 supplied by Micromeritics Co.), it was found that in fine pores having a pore diameter of 100 to 75,000 Å, the pore volume was 0.61 cc/g-shaped catalyst and the median pore diameter based on the pore volume was 2,900 Å. Note, the average sedimentation velocity of the catalyst A in monochlorobenzene was 0.75 cm/sec.

In order to evaluate the catalyst A as the shaped zeolite catalyst, liquid phase chlorination of monochlorobenzene (hereinafter referred to as "MCB") was carried out. The liquid phase chlorination was continuously conducted by using a Pyrex vessel type reactor having an inner diameter of 55 mm and a volume of 400 ml equipped with a stirrer, a condenser and a catalyst-separating cylindrical circulator having an inner diameter of 25 mm and a height of 70 mm. The reactor was charged with 250 g of MCB and 20 g of the catalyst A and heated by using an oil bath. Chlorine gas was continuously supplied through a blow tube into the reactor and MCB was continuously supplied into the reactor by a metering pump while the reaction mixture was stirred. The reaction temperature was 100° C., the feed rate of MCB was 117.8 mole/kg-catalyst·hour and the chlorine feed rate was 58.9 mole/kg-catalyst·hour. The reaction liquid was allowed to overflow from the catalyst-separating circulator and was periodically analyzed by gas chromatography. It was found that the catalyst was uniformly dispersed in the reaction vessel, and the conversion of chlorine at the initial stage of the reaction was 98.9%. In the catalyst-separating circulator, the catalyst was sufficiently sedimented and little powdering or flow-out of the catalyst by abrasion was observed. Even after the passage of 100 hours, the conversion of chlorine was 98.9%.

EXAMPLE 2

In water, 100 parts of a powder of L type zeolite was sufficiently mixed with 15 parts, as calculated as silica, of a silica sol ($SiO_2=30\%$, supplied by Shokubai Kasei) to prepare a slurry having a solid concentration of 50%. The slurry was spray-dried and granulated in the same manner as described in Example 1 to obtain a shaped zeolite catalyst. The particle diameter distribution of the solids in the wet-pulverized slurry was such that the amount of particles having a particle diameter of at least 30 $\mu$m was 8%. After calcination at 600° C. for one hour, a catalyst B having a particle diameter of 74 to 297 $\mu$m (74−177 $\mu$m=57.3%, 177 −297 $\mu$m=42.7%) was obtained by sieving. In fine pores of the catalyst B having a pore diameter of 100 to 75,000 Å, the pore volume was 0.41 cc/g-shaped catalyst, and the median pore diameter was 1,800 Å. The average sedimention velocity of the catalyst B in MCB was 0.80 cm/sec.

The liquid phase chlorination of MCB was carried out in the same manner as described in Example 1 by using 20 g of the catalyst B. The catalyst was uniformly dispersed in the reactor and the conversion of chlorine was 98.3% at the initial stage of the reaction. The catalyst was promptly sedimented in the catalystseparating cylindrical circulator and little flow-out of the catalyst was observed. Even after passage of 20 hours, the conversion of chlorine was 98.1%.

EXAMPLE 3

A shaped zeolite catalyst was prepared by carrying out spray-drying granulation in the same manner as described in Example 1 except that the amount added of acid clay was changed to 15 parts per 100 parts of L type zeolite. The solids in the wet-pulverized slurry had such a particle diameter distribution that the amount of particles having a particle diameter of at least 30 $\mu$m was 3%. After calcination at 600° C. for 1 hour, a catalyst C having a particles diameter of 74 to 297 $\mu$m (74—177 $\mu$m=51.6%, 177—297 $\mu$m=48.4%) was obtained by sieving. In fine pores of the catalyst C having a pore size of 100 to 75,000 Å, the pore volume was 0.68 cc/g-shaped catalyst, and the median pore diameter was 3,700 Å. The average sedimentation velocity of the catalyst C in MCB was 0.68 cm/sec.

Liquid phase chlorination of MCB was carried out in the same manner as described in Example 1 by using 20 g of the catalyst C. The catalyst was uniformly dispersed in the reactor and the conversion of chlorine was 99.0% at the initial stage of the reaction. The catalyst was sufficiently sedimented in the catalyst-separating circulator, and little powdering or flow-out of the catalyst by abrasion was observed. Even after passage of 50 hours, the conversion of chlorine was 99.0%.

EXAMPLE 4

In water, 100 parts of a powder of L type zeolite was sufficiently mixed with 30 parts of kibushi clay to prepare a slurry having a solid concentration of 35%. A shaped zeolite catalyst was obtained by carrying out spray-drying granulation in the same manner as described in Example 1. The particle diameter distribution of the solids in the wet-pulverized slurry was such that the amount of particles having a particle diameter of at least 30 $\mu$m was 2%. After calcination at 600° C. for 1 hour, a catalyst D having a particle diameter of 74 to 297 $\mu$m (74—177 $\mu$m=47.9%, 177—297 $\mu$m =52.1%) was obtained by sieving. In fine pores of the catalyst D having a pore diameter of 100 to 75,000 Å, the pore volume was 0.57 cc/g-shaped catalyst, and the median pore diameter was 2,600 Å. The average sedimentation velocity of the catalyst D in MCB was 0.78 cm/sec.

Liquid phase chlorination of MCB was carried out in the same manner as described in Example 1 by using the catalyst D. The catalyst was uniformly dispersed in the reactor, and the conversion of chlorine was 98.2% at the initial stage of the reaction. The catalyst was sufficiently sedimented in the catalyst-separating cylindrical circulator and little powdering or flow-out of the catalyst by abrasion was observed. Even after the passage of 50 hours, the conversion of chlorine was 98.2%.

COMPARATIVE EXAMPLE 1

A powder of L type zeolite was directly calcined at 600° C. for 1 hour, and liquid phase chlorination reaction of MCB was carried out in the same manner as described in Example 1 by using the calcination product. The catalyst was uniformly dispersed in the reactor, and the conversion of chlorine was 99.1% at the initial stage of the reaction. The separability of the catalyst in the catalyst-separating cylindrical circulator was poor and flow-out of the catalyst with the reaction liquid was observed. The amount of the catalyst which had flowed out in 10 hours from the start of the reaction was 10.3 g, and the conversion of chlorine after the passage of 10 hours was reduced to 97.2%. The sedimentation velocity of this comparative catalyst in MCB was lower than 0.2 cm/sec.

COMPARATIVE EXAMPLE 2

Spray-drying granulation was carried out in the same manner as described in Example 1 except that the slurry prepared in Example 1 was not passed through the wet pulverizer. When the particle diameter distribution of the solids in the slurry was measured by a Coulter counter, it was found that particles having a particle diameter of at least 30 $\mu$m were present in an amount of 35%. The obtained shaped zeolite catalyst was calcined at 600° C. for 1 hour, and a catalyst E having a particle diameter of 74 to 297 $\mu$m (74—177 $\mu$m=38.5%, 177 —297 $\mu$m=61.5%) was obtained by sieving. In fine pores of the catalyst E having a pore diameter of 100 to 75,000 Å, the pore volume was 0.63 cc/g-shaped catalyst, and the median pore diameter was 5,800 Å. The average sedimentation velocity of the catalyst in MCB was 0.71 cm/sec.

Liquid phase chlorination reaction of MCB was carried out in the same manner as described in Example 1 by using 20 g of the catalyst E. The catalyst E was uniformly dispersed in the reaction vessel, and the conversion of chlorine was 99.1% at the initial stage of the reaction. With the lapse of time, the catalyst was powdered and flow-out of the catalyst was observed. The amount of the catalyst which had flowed out in 50 hours from the start of the reaction was 10.5 g, and at that point, the conversion of chlorine was reduced to 98.0%.

COMPARATIVE EXAMPLE 3

In a kneading machine, 100 parts of a powder of L type zeolite was sufficiently mixed and humidified with 25 parts of acid clay, and the kneaded mixture was extruded through a screen having a mesh size of 0.5 mm and shaped into spheres by rolling-granulation method. The shaped catalyst was dried at 130° C. for 15 hours and calcined at 600° C. for 1 hour. A catalyst F having a particle diameter of 250 to 350 $\mu$m (250—297 $\mu$m=26%, 297—350 $\mu$m=74%) was obtained by sieving. In fine pores of the catalyst F having a pore diameter of 100 to 75,000 Å, the pore volume was 0.34 cc/g-shaped catalyst, and the median pore diameter was 1,100 Å. The average sedimentation velocity of the catalyst F in MCB was 2.2 cm/sec.

Liquid phase chlorination of MCB was carried out in the same manner as described in Example 1 by using 20 g of the catalyst F. The shaped zeolite catalyst was not uniformly dispersed in the reaction vessel, and the conversion of chlorine was as low as 90.5%.

COMPARATIVE EXAMPLE 4

In a kneading machine, 100 parts of a powder of L type zeolite was sufficiently mixed and humidified with 25 parts of Kibushi clay, and the kneaded mixture was extruded through a die having holes having a diameter of 1.5 mm and dried at 130° C. for 15 hours. Then, the size of the shaped catalyst was adjusted to a diameter of 1.5 mm and a length of 5 mm, and the shaped catalyst was calcined at 600° C. for 1 hour to obtain a catalyst G. When the catalyst G was measured by a mercury pressure porosimeter, it was found that in fine pores having a pore diameter of 100 to 75,000 Å, the pore volume was 0.35 cc/g-shaped catalyst, and the median pore diameter was 800 Å. The sedimentation velocity of the catalyst in MCB was higher than 10 cm/sec.

Liquid phase chlorination of MCB was carried out in the same manner as described in Example 1 by using 20 g of the catalyst G. The shaped zeolite catalyst was not uniformly dispersed in the reactor, and the conversion of chlorine was as low as 88.7%.

COMPARATIVE EXAMPLE 5

The shaped zeolite catalyst prepared in Comparative Example 4 was crushed in a mortar and a catalyst H having a particle diameter of 177 to 297 μm was obtained by sieving.

Liquid phase chlorination of MCB was carried out in the same manner as described in Example 1 by using 20 g of the catalyst H. The shape of the catalyst H was not spherical. The catalyst H was uniformly dispersed in the reactor, but the conversion of chlorine at the initial stage of the reaction was as low as 96.2%. Since the sedimentability of the catalyst in the catalyst-separating cylindrical circulator was poor, flow-out of the catalyst with the reaction liquid was observed. The amount of the catalyst which had flowed out in 20 hours from the start of the reaction was 7.3 g, and at that point, the conversion of chlorine was reduced to 93.6%. The sedimentation velocity of the catalyst H in MCB was 1.0 cm/sec.

COMPARATIVE EXAMPLE 6

The shaped zeolite catalyst obtained by spray-drying in Example 1 was classified to obtain a catalyst I having a particle diameter of 53 to 88 μm (53−74 μm =32.5%, 74−88 μm=67.5%). The average sedimentation velocity of the catalyst I in MCB was 0.25 cm/sec.

Liquid phase chlorination of MCB was carried out in the same manner as described in Example 1 by using 20 g of the catalyst I. The catalyst was uniformly dispersed in the reactor and the conversion of chlorine was 99.0% at the initial stage of the reaction. The sedimentability of the catalyst in the catalyst-separating cylindrical circulator was poor and flow-out of the catalyst with the reaction liquid was observed. The amount of the catalyst which had flowed out in 20 hours from the start of the reaction was 5.2 g, and at the point, the conversion of chlorine was reduced to 98.2%.

COMPARATIVE EXAMPLE 7

In a kneader, 100 parts of a powder of L type zeolite was sufficiently mixed with 20 parts, as calculated as silica, of a silica sol while adjusting the water content, and the kneaded mixture was extruded through a die having holes having a diameter of 1.5 mm and dried at 130 ° C. for 15 hours. The size of the shaped form was adjusted to a diameter of 1.5 mm and a length of 4 mm and the shaped form was calcined at 600° C. for 1 hour to obtain a catalyst J. In fine pores of the catalyst J having a pore diameter of 100 to 75,000 Å, the pore volume was 0.29 cc/g-shaped catalyst, and the median pore diameter was 1,000 Å.

Liquid phase chlorination of MCB was carried out in the same manner as described in Example 1 by using 20 g of the catalyst J. The catalyst J was not uniformly dispersed in the reactor, and the conversion of chlorine was as low as 88.5%. The sedimentation velocity of the catalyst J in MCB was 10 cm/sec.

COMPARATIVE EXAMPLE 8

The catalyst J prepared in Comparative Example 7 was crushed in a mortar and classified to obtain a catalyst K having a particle diameter of 105 to 297 μm, and liquid phase chlorination of MCB was carried out in the same manner as described in Example 1 by using this catalyst but the conversion of chlorine at the initial stage of the reaction was as low as 95.1%. The sedimentation velocity of the catalyst K in MCB was 0.65 cm/sec.

EXAMPLE 5

In water, 100 parts of a powder of commercially available Y type zeolite (supplied by Tosoh) was sufficiently mixed with 20 parts of acid clay to obtain a slurry having a solid concentration of 30%. The slurry was passed through a wet pulverizer, introduced into a spray-drying granulator and shaped into a granular form by using hot air maintained at 100° C. The solids in the wet-pulverized slurry had a particle diameter distribution such that the amount of particles having a particle diameter of at least 30 μm was 6%. The shaped body was calcined at 600° C. for 1 hour and classified to obtain a catalyst M having a particle diameter of 74 to 297 μm (74−177 μm=57.3%, 177−297 μm =42.7%). In fine pores of the catalyst M having a pore diameter of 100 to 75,000 Å, the pore volume was 0.84 cc/g-shaped catalyst, and the median pore diameter was 5,200 Å. The sedimentation velocity of the catalyst M in MCB was 0.58 cm/sec.

Liquid phase chlorination of MCB was carried out in the same manner as described in Example 1 by using 15 g of the catalyst M. The catalyst was uniformly dispersed in the reactor, and the conversion of chlorine was 99.5% at the initial stage of the reaction. The catalyst was promptly sedimented in the catalyst-separating cylindrical circulator and little flow-out of the catalyst was observed. Even after the passage of 100 hours, the conversion of chlorine was 99.4%.

COMPARATIVE EXAMPLE 9

The slurry prepared in Example 5 was spray-dried and calcined in the same manner as described in Example 5 except that the slurry was not passed through the wet pulverizer, and the shaped form was classified to obtain a catalyst N having a particle diameter of 74 to 297 μm (74−177 μm=30.5%, 177−297 μm =69.5%). The solids in the slurry that was not wet-pulverized had a particle diameter distribution such that the amount of particles having a particle diameter of at least 30 μm was 15%. In fine pores of the catalyst N having a pore diameter of 100 to 75,000 Å, the pore volume was 1.1 cc/g-shaped catalyst, and the median pore diameter was 8,100 Å. The average sedimentation speed of the catalyst N in MCB was 0.55 cm/sec.

Liquid phase chlorination of MCB was carried out in the same manner as described in Example 1 by using 15 g of the catalyst N. The catalyst was uniformly dispersed in the reactor, and the conversion of chlorine was 99.6% at the initial stage of the reaction. With the lapse of time, the catalyst was powdered by abrasion and flow-out of the catalyst was observed. When 50 hours had passed from the start of the reaction, the flow-out amount of the catalyst reached 11.5 g and the conversion of chlorine was reduced to 98.1%.

I claim:

1. A process for producing a compound comprising chlorine and benzene comprising the step of reacting at least one of benzene and a mono halobenzene with a chlorine-containing halogenation agent in a liquid solvent, and in the presence of a shaped zeolite catalyst in an amount of 0.001 to 1 kg zeolite per liter of the solvent at a temperature of 0° C. to 200° C. and a pressure sufficient to induce reaction, wherein said catalyst is composed of substantially spherical particles having a particle diameter substantially in the range of 70 to 300 m, and which has fine pores having a pore volume of from 0.4 to 1 cc per gram of the shaped catalyst and a median pore diameter based on the pore volume of 1,000 to 5,500 angstroms, as measured by mercury porosimetry on pores having a pore diameter of from 100 to 75,000 angstroms.

2. A process according to claim 1, wherein the shaped zeolite catalyst consists essentially of at least 20% by weight of a zeolite and up to 80% by weight of a binder.

3. A process according to claim 1 wherein the shaped zeolite catalyst is prepared by a spray-drying granulation method wherein a zeolite-containing slurry is sprayed in hot air to form liquid drops and dry the liquid drops.

4. A process according to claim 3 wherein the zeolite-containing slurry contains the solid particles in which not more than 10% by weight of particles based on the total particles have a particle diameter of at least 30 μm as measured by the Coulter counter method, and said slurry has a solid concentration of 20 to 60% by weight.

5. A process according to claim 1 wherein the shaped zeolite catalyst has been calcined at a temperature of 250° to 900° C.

6. A process according to claim 1 wherein the shaped zeolite catalyst is made of zeolite L or zeolite Y.

7. A process according to claim 1 wherein the monohalobenzene is monochlorobenzene.

8. A process according to claim 1 wherein the shaped zeolite catalyst is prepared by the steps of:
  (a) preparing a slurry containing a solid which consists essentially of at least 20% by weight of a zeolite and up to 80% by weight of a binder,
  (b) wet-pulverizing the slurry to reduce the particle size of the zeolite to an extend such that the amount of particles having a diameter of at least 30 μm as measured by the Coulter counter method is not more than 10% by weight based on the total particle weight,
  (c) spraying the slurry in hot air at a temperature of 60° C. to 200° C. to form liquid drops,
  (d) drying the liquid drops to form catalyst particles, and
  (e) calcining the catalyst particles at a temperature of 250° C. to 900° C.

9. A process according to claim 1 wherein the chlorination of benzene or a monohalobenzene is carried out in a batchwise or semi-batchwise manner in the reaction medium using 1 to 1,500 mol/kg-cat.hr of chlorine gas as a chlorinating agent and the concentration of reactants in the reaction medium is in the range of 5 to 99% by weight.

10. A process according to claim 1 wherein the chlorination of benzene or a monohalobenzene is carried out in a continuous manner in the reaction medium while 0.5 to 300 l/kg-cat.hr of liquid reactants and 1 to 1,500 mol/kg-cat.hr of chlorine gas are supplied to the reaction medium as a chlorinating agent, and the concentration of the starting reactants in the reaction medium is in the range of 5 to 99% weight.

11. A process for producing a compound comprising halogen and benzene comprising the step of reacting at least one of benzene and a mono halobenzene with a halogenation agent in a liquid solvent, and in the presence of a shaped zeolite catalyst in an amount of 0.001 to 1 kg zeolite per liter of the solvent at a temperature of 0° C. to 200° C. and a pressure sufficient to induce reaction, wherein said catalyst is composed of substantially spherical particles having a particle diameter substantially in the range of 70 to 300 m, and which has fine pores having a pore volume of from 0.4 to 1 cc per gram of the shaped catalyst and a median pore diameter based on the pore volume of 1,000 to 5,500 angstroms, as measured by mercury porosimetry on pores having a pore diameter of from 100 to 75,000 angstroms.

* * * * *